United States Patent
Herrmann et al.

(10) Patent No.: US 7,696,247 B2
(45) Date of Patent: Apr. 13, 2010

(54) LIPID-BASED NITRIC OXIDE DONORS

(75) Inventors: Robert A. Herrmann, Boston, MA (US); Wendy Naimark, Cambridge, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1591 days.

(21) Appl. No.: 10/885,055

(22) Filed: Jul. 6, 2004

(65) Prior Publication Data

US 2004/0259840 A1  Dec. 23, 2004

Related U.S. Application Data

(62) Division of application No. 09/745,226, filed on Dec. 21, 2000, now Pat. No. 6,780,849.

(51) Int. Cl.
| | | |
|---|---|---|
| A61K 31/20 | (2006.01) | |
| A01N 33/26 | (2006.01) | |
| C07C 205/00 | (2006.01) | |
| C07C 207/00 | (2006.01) | |
| C07C 241/00 | (2006.01) | |
| C07C 243/00 | (2006.01) | |

(52) U.S. Cl. ...................... 514/558; 514/611; 562/434; 564/112

(58) Field of Classification Search ........................ None
See application file for complete search history.

(56) References Cited

U.S. PATENT DOCUMENTS

| | | | | |
|---|---|---|---|---|
| 4,466,914 A | | 8/1984 | Hazen et al. ................ | 540/200 |
| 5,137,919 A | | 8/1992 | Igarashi et al. ............. | 514/642 |
| 5,185,376 A | | 2/1993 | Diodati et al. ............. | 514/611 |
| 5,519,020 A | | 5/1996 | Smith et al. ................ | 424/718 |
| 5,583,101 A | | 12/1996 | Stamler et al. ................ | 514/2 |
| 5,698,738 A | | 12/1997 | Garfield et al. ............. | 564/112 |
| 5,700,830 A | | 12/1997 | Korthuis et al. ............. | 514/426 |
| 5,721,365 A | | 2/1998 | Keefer et al. ................ | 544/382 |
| 5,741,893 A | | 4/1998 | Hsia ........................... | 530/385 |
| 5,767,089 A | | 6/1998 | Hsia ........................... | 514/21 |
| 5,770,645 A | | 6/1998 | Stamler et al. ............. | 524/419 |
| 5,814,666 A | | 9/1998 | Green et al. ................ | 514/611 |
| 5,824,669 A | | 10/1998 | Garvey et al. ............. | 514/174 |
| 5,824,781 A | | 10/1998 | Hsia ........................... | 530/385 |
| 5,863,890 A | | 1/1999 | Stamler et al. ................ | 514/2 |
| 5,869,104 A | | 2/1999 | Taylor et al. ................ | 424/680 |
| 5,891,472 A | | 4/1999 | Russell ........................ | 424/484 |
| 6,045,827 A | * | 4/2000 | Russell ........................ | 424/485 |
| 6,087,479 A | | 7/2000 | Stamler et al. ............. | 530/363 |
| 6,147,068 A | | 11/2000 | Smith et al. ................ | 514/182 |

FOREIGN PATENT DOCUMENTS

| | | |
|---|---|---|
| WO | 98/08496 A1 | 3/1998 |
| WO | WO 00/49993 | 8/2000 |
| WO | WO 00/53193 | 9/2000 |

OTHER PUBLICATIONS

Kennedy, SD et al., "Measurement of in vitro P-selection expression by flow cytometry", Am J Clin Pathol., Jan. 1997, vol. 107, No. 1, pp. 99-104.
Campbell, B. et al., "Beneficial effects of N,N,N-trimethylsphingosine following ischemia and reperfusion in the isolated perfused rat heart", Cardiovasc Res., Aug. 1998, vol. 39, No. 2, pp. 393-400.
Mowery, KA, et al., "Preparation and characterization of hydrophobic polymeric films that are thromboresistant via nitric oxide release", Biomaterials, Jan. 2000, vol. 21, No. 1, pp. 9-21.
Schaffer, MR et al., "Nitric oxide regulates wound healing", J Surg Res, Jun. 1996, vol. 63, No. 1, pp. 237-240.
Akcay, MN et al., "Effect of nitric oxide synthase inhibitor on experimentally induced burn wounds", J Trauma, Aug. 2000, vol. 49, No. 2, pp. 327-330.
Hirata, K. et al., "Regulated expression of endothelial cell-derived lipase", Biochem Biophys Res Commun, May 27, 2000, vol. 272, No. 1, pp. 90-93.

(Continued)

*Primary Examiner*—Traviss C McIntosh, III
(74) *Attorney, Agent, or Firm*—Mayer & Williams PC; David B. Bonham

(57) ABSTRACT

Novel nitric-oxide releasing lipid molecules are provided which comprise a lipid molecule selected from (a) phosphoglycerides, (b) lipids having a sphingosine base as a backbone, (c) monoacylglycerols, (d) diacylglycerols, (e) glycosylacylglycerols, and (f) sterol compounds of the formula:

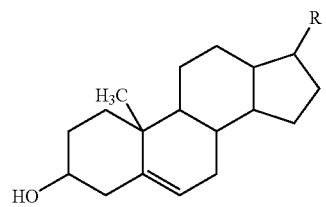

where R is a branched aliphatic chain of eight or more carbon atoms, wherein the lipid molecule is provided with a nitric-oxide containing group which comprises (a) a —S—N=O moiety, (b) a —O—N=O moiety, or (c) a

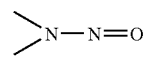

a moiety. Also provided are methods of forming such nitric oxide releasing lipid molecules.

Various pharmaceutical compositions, topical liquids and drug delivery systems comprising the nitric-oxide releasing lipid molecules are also described. Further provided are methods for therapeutically administering nitric oxide to patients, methods of treating or preventing various conditions, methods for promoting wound healing and methods of reducing the cells present in an atherosclerotic lesion, which methods utilize the nitric-oxide releasing lipid molecules.

23 Claims, No Drawings

OTHER PUBLICATIONS

Bettelheim et al., Introduction to Organic and Biochemistry, 4th ed., Harcourt College Publishers, 1990, p. 233.

Michael P. Doyle et al., "Hydrolysis, Nitrosyl Exchange, and Synthesis of Alkyl Nitrites", J. Org. Chem. 1983, 48, 3379-3382.

Sidney S. Mirvish et al., "Identification of Cholesterol as a Mouse Skin Lipid that Reacts with Nitrogen Dioxide to Yield a Nitrosating Agent, and of Cholesteryl Nitrite as the Nitrosating Agent Produced in a Chemical System from Cholesterol", Cancer Letters, 31 (1986), 97-104.

* cited by examiner

LIPID-BASED NITRIC OXIDE DONORS

STATEMENT OF RELATED APPLICATION

This is a divisional application and claims the benefit of priority of U.S. patent application Ser. No. 09/745,226, filed Dec. 21, 2000, now U.S. Pat. No. 6,780,849, entitled "Lipid-Based Nitric Oxide Donors," the entire specification of which is incorporated by reference herein.

FIELD OF THE INVENTION

The present invention relates to lipid-based nitric oxide donors and more particularly to lipids having one or more of the following groups: (a) S-nitroso groups, (b) O-nitroso-groups, and (c) N-nitroso groups.

BACKGROUND OF THE INVENTION

Nitric oxide can be used therapeutically in a number of ways. At high concentrations, nitric oxide is cytotoxic and may be used to reduce the numbers of undesirable cells, such as cancer cells, bacterial cells and cells present in atherosclerotic lesions. At lower concentrations, nitric oxide may promote the health of certain cells and tissue.

Compounds that contain S-nitroso groups, O-nitroso-groups, and N-nitroso groups are all known to release nitric oxide.

O-nitroso compounds are compounds having one or more —O—NO groups, and are also referred to as O-nitrosylated compounds and nitrite compounds.

S-nitroso compounds are compounds with one or more —S—NO groups and are also referred to as nitrosothiols and S-nitrosylated compounds. An —S—NO group is also referred to in the art as a sulfonyl nitrite, a thionitrous acid ester, an S-nitrosothiol or a thionitrite.

Compounds having an =N—NO group are referred to herein as N-nitroso compounds. Common examples are compounds having —N—N$_2$O$_2^-$ groups (see structure below), which are known in the art as nonoate compounds, and more specifically as N-nonoate compounds.

Examples of the above three classes of compounds can be found, for example, in U.S. Pat. Nos. 5,583,101 and 5,814,666, the entire disclosures of which are hereby incorporated by reference.

U.S. Pat. No. 5,824,669 and WO 00/49993, which are herein incorporated by reference, describe nitrosated and nitrosylated steroids. Further information can be found within these documents.

U.S. Pat. No. 5,767,089 (the '089 patent), the disclosure of which is hereby incorporated by reference, discloses among other things nitroxide-labeled macromolecules, including hemoglobin, albumin, immunoglobulins and liposomes. See, e.g., Abstract and Col. 1, lines 13 et seq. For further information, see the disclosure of the '089 patent (see, also, U.S. Pat. Nos. 5,824,781 and 5,741,893).

SUMMARY OF THE INVENTION

The present invention is directed to a new class of S-nitrosylated, N-nitrosylated and/or O-nitrosylated lipid molecules.

According to an embodiment of the invention, novel nitric-oxide releasing lipid molecules are provided which comprise a lipid molecule selected from (a) phosphoglycerides, (b) lipids having a sphingosine base as a backbone, (c) monoacylglyerols, (d) diacylglycerols, (e) glycosylacylglycerols, and (f) sterol compounds of the formula:

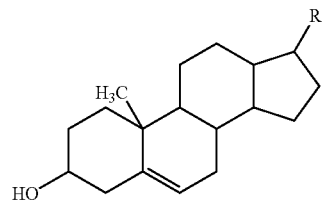

where R is a branched aliphatic chain of eight or more carbon atoms, wherein the lipid molecule is provided with a nitric-oxide containing group, which comprises (a) a

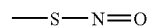

moiety, (b) a

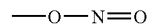

moiety, or (c) a

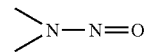

moiety.

Preferred lipids having a sphingosine base as a backbone include N,N,N-trimethylsphingosine and sphingolipids, such as gangliosides. Preferred phosphoglycerides include phosphatidylinositol and phosphatidylcholine. Cholesterol is a preferred sterol molecule. A preferred

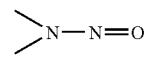

moiety is the

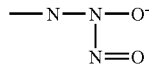

moiety and more preferably the

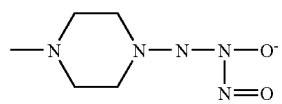

moiety.

The pharmaceutical compositions comprising the nitric-oxide releasing lipid molecules of the present invention contain varying amounts of the lipid molecules, for example, at least 0.001 wt %, at least 0.01 wt %, at least 0.1 wt %, at least 1 wt %, at least 10 wt %, or at least 90 wt %.

In other embodiments of the invention, methods of forming a nitric oxide releasing lipid molecule is provided. These methods comprise:

(1) providing a lipid molecule having a nucleophilic moiety selected from a thiol moiety, an amine moiety and an alcohol moiety, the lipid molecule selected from (a) phosphoglycerides, (b) lipids having a sphingosine base as a backbone, (c) monoacylglyerols, (d) diacylglycerols, (e) glycosylacylglycerols, and (f) sterol compounds of the formula:

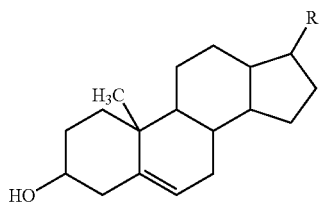

where R is a branched aliphatic chain of eight or more carbon atoms; and (2) supplying the lipid molecule with a nitric-oxide containing group at a position corresponding to the nucleophilic moiety, wherein the nitric-oxide containing group comprises a

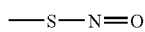

moity, a

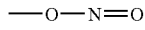

moity, or a

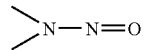

moiety.

In many preferred embodiments of the invention, an alcohol moiety on the lipid molecule is converted to a group comprising a thiol moiety before supplying the lipid molecule with the nitric-oxide containing group, which can be, for example, a nitric-oxide containing group comprising an

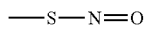

moiety.

In some embodiments, the nitric-oxide releasing lipid molecules of the present invention are provided in a topical liquid, such as a solution, dispersion, spray, lotion, gel, cream or ointment.

Other embodiments are directed to a drug delivery system comprising a medical article and the nitric-oxide releasing lipid molecules of the present invention. Preferred medical articles include (a) a bandage or a patch and (b) an intravascular medical device, such as a balloon catheter, an injection catheter, an infusion catheter, a stent, a stent graft, or a distal protection device.

The nitric-oxide releasing lipid molecules associated with the drug delivery system can be, for example, (a) provided within a polymer matrix, preferably a biocompatible matrix selected from a stable polymer matrix and a biodegradable polymer matrix, (b) dissolved or dispersed in a solution, (c) adsorbed on a tissue-contacting surface of the medical article, or (d) provided within a micelle or a liposome.

The drug delivery system in some embodiments will further comprise a therapeutically effective amount of an auxiliary therapeutic agent, such as an agent having antineoplastic activity, an agent having antiproliferative activity, or an agent having both antineoplastic and antiproliferative activity.

According to another embodiment of the present invention, a method for therapeutically administering nitric oxide to a patient is provided. The method comprises administering the nitric-oxide releasing lipid molecules of the invention to a patient. Preferred routes of administration include (a) topical administration routes, (b) administration routes in which the nitric-oxide containing lipid molecules are administered within the body, for example, by implantation, via an intravascular delivery device (e.g., a balloon catheter, an injection catheter, an infusion catheter, a stent, a stent graft, or a distal protection device) or via a direct injection route.

According to other embodiments of the invention, methods of treating or preventing various conditions are provided. These methods comprise administering an amount of the nitric-oxide releasing lipid molecules of the invention effective to treat or prevent the condition. Preferred conditions include atherosclerosis, myocardial infarction, restenosis, peripheral vascular disease, stroke, impotence, septic shock, arthritis, cancer, bacterial infection, impetigo, epidermolysis bullosa, eczema, neurodermatitis, psoriasis, pruritis, erythema, hidradenitis suppurativa, warts, diaper rash, and jock itch.

In other embodiments of the invention, the nitric-oxide releasing lipid molecules are used to promote wound healing in a patient or to reduce the cells present in an atherosclerotic lesion in a patient.

One advantage of the present invention is that nitric oxide releasing compounds with lipophilic or amphiphilic characteristics are provided.

Another advantage of the present invention is that nitric oxide releasing compounds are provided which can be readily incorporated into lipophilic tissue, promoting tissue uptake and enhancing tissue retention time.

Another advantage of the present invention is that nitric oxide releasing compounds are provided which can be readily incorporated into a cell membrane, promoting cell uptake and enhancing cell retention time.

These and other embodiments and advantages of the present invention will become readily apparent to those of ordinary skill in the art upon review of the description and claims to follow.

DETAILED DESCRIPTION OF THE INVENTION

The present invention provides a new class of lipid molecules, which lipid molecules are provided with one or more nitric-oxide containing groups. The nitric-oxide containing groups comprises one or more of the following moieties:

(a) an S-nitroso moiety

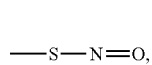

(b) an O-nitroso moiety

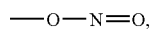

and/or (c) an N-nitroso moiety

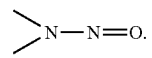

Preferred N-nitroso groups include the N-nonoates,

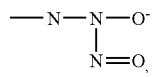

a class of compounds that includes substituted piperazines

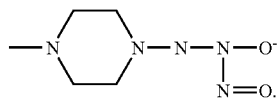

As is well known in the art, pendant S-nitroso-, N-nitroso- and O-nitroso-groups can be made, for example, from pendant thiols, amines and alcohols.

Because many naturally occurring lipid compounds do not contain thiol groups, in some embodiments of the present invention (for example, those in which an S-nitroso moiety is formed), it is desirable to provide a lipid species with pendant thiol groups from a lipid species having one or more pendant nucleophilic groups, such as alcohols or amines. These pendant nucleophilic groups can be converted to pendant thiol groups by methods known in the art, such as those disclosed in Gaddell and Defaye, Angew. Chem. Int. Ed. Engl. 30: 78 (1991) and Rojas et al., J. Am. Chem. Soc. 117: 336 (1995), the teachings of which are hereby incorporated into this application by reference. In these methods, primary alcohols are thiolated preferentially over secondary alcohols.

Moreover, U.S. Pat. No. 5,770,645, the entire disclosure of which is hereby incorporated by reference, teaches that a polythiolated species can be prepared by reacting a polyhydroxylated species, and preferably primary alcohol groups of a polyhydroxylated species, with a reagent that adds a moiety containing a free thiol or protected thiol to the alcohol. In one example the polysaccharide is reacted with a bis isocyanatoalkyldisulfide followed by reduction to functionalize the alcohol as shown in Structural Formula (I):

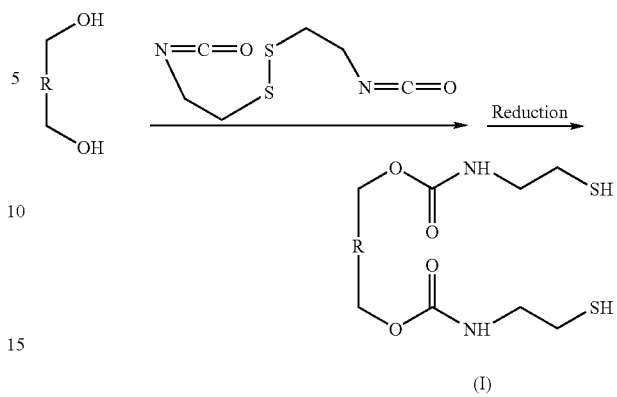

Conditions for carrying out this reaction are found in Cellulose and its Derivatives, Fukamota, Yamada and Tonami, Eds. (John Wiley & Sons), Chapter 40, (1985), the disclosure of which is incorporated herein by reference.

Methods for producing thiol groups from alcohol groups are also disclosed in U.S. Pat. No. 4,466,914, the disclosure of which is incorporated herein by reference.

Lipids with thiol groups are also available commercially. One example is phosphatidylthioethanol available from Avanti Polar Lipids, 700 Industrial Drive, Alabaster, Ala. 35007.

Once a lipid with one or more pendant thiol groups is provided, these compounds can be reacted with a nitrosylating agent under conditions suitable for nitrosylating the free thiol groups. Appropriate procedures are discussed, for example, in U.S. Pat. No. 5,770,645. Nitrosylating agents disclosed as suitable include acidic nitrite, nitrosyl chloride, compounds comprising an S-nitroso group (S-nitroso-N-acetyl-D,L-penicillamine (SNAP), S-nitrosoglutathione (SNOG), N-acetyl-S-nitrosopenicillaminyl-S-nitrosopenicillamine, S-nitrosocysteine, S-nitrosothioglycerol, S-nitrosodithiothreitol and S-nitrosomercaptoethanol), an organic nitrite (e.g. ethyl nitrite, isobutyl nitrite, and amyl nitrite), peroxynitrites, nitrosonium salts (e.g. nitrosyl hydrogen sulfate), oxadiazoles (e.g. 4-phenyl-3-furoxancarbonitrile) and the like. For more information, see U.S. Pat. No. 5,770,645.

Similar procedures are known in the art for the formation of other groups, including N-nitroso-groups (see, e.g., U.S. Pat. No. 5,185,376, the disclosure of which is incorporated herein by reference) and N-nonoates (see, e.g., U.S. Pat. Nos. 5,721,365, 5,698,738 and 5,519,020, the disclosures of which are incorporated herein by reference).

Using the above as well as other well-known procedures, a wide range of S-nitroso-, N-nitroso- and O-nitroso-lipids can be produced from appropriate precursor molecules in accordance with the present invention, several of which are discussed below.

Exemplary precursor molecules appropriate for the practice of the present invention include lipids having a sphingosine base as a backbone. By "a sphingosine base" is meant sphingosine as well as related bases known in the art such as dihydrosphingosine, phytosphingosine, 4,8-sphingadiene, and so forth.

In addition to sphingosine bases themselves, other lipids having a sphingosine base as a backbone are appropriate for the practice of the present invention, including N-alkyl-substituted sphingosine bases such as N,N,N-trimethylsphingosine. N,N,N-trimethylsphingosine is known to inhibit platelet activation, S. D. Kennedy, Y. Igarashi and T. S. Keckler, 1997 "Measurement of in vitro P selectin expression by flow cytometry," Am. J. Clin. Pathol., 1:107, pp. 99-104, the disclosure of which is hereby incorporated by reference. It also prevents leukocyte-endothelial interactions and preserves cardiac contractile function following myocardial ischemia and reperfusion, B. Campbell and Y. K. Shin, R. Scalia and A. M. Lefer, 1998, "Beneficial effects of N,N,N-trimethylsphingosine following ischemia and reperfusion in the isolated perfused rate heart," Cardiovasc. Res. 2:39, pp. 393-400, the disclosure of which is hereby incorporated by reference. It further inhibits tumor growth and protein kinase C.

Still other lipids having a sphingosine base as a backbone are appropriate for the practice of the present invention and include the sphingolipids, which are complex lipids containing three characteristic building block components: (1) a polar head group, (2) a fatty acid molecule, and (3) a sphingosine base as a backbone. Exemplary groups of sphingolipids appropriate for the practice of the invention include sphingomyelins, neutral glycosphingolipids (including cerebrosides) and acidic glycosphingolipids. Acidic glycosphingolipids, also known as gangliosides, are present in neurological tissue. Sphingolipids contain, for example, —OH groups for nitrosylation, with the glycosphingolipids having an abundant supply of —OH groups as they contain saccharide moieties within their head groups.

Phosphoglycerides are other precursor molecules appropriate for the practice of the present invention. Preferred phosphoglycerides are those having one or more —OH groups in the polar head (for example, phosphatidylinositol, phosphatidylglycerol and cardiolipin), those with amine groups in the polar head (for example, phosphatidylcholine, phosphatidylethanolamine and phosphatidylserine) and those with both —OH and amine groups in the polar head (for example, 3'—O-lysylphosphatidylglycerol). Of these, phosphatidylinositol (which is an important intracellular signaling lipid) and phosphatidylcholine are highly preferred.

Sterols, i.e., molecules of the following structure:

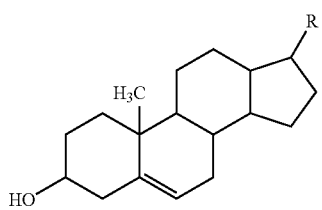

where R is a branched aliphatic chain of eight or more carbon atoms, are also appropriate as precursor molecules for the practice of the present invention. A preferred sterol is cholesterol.

Other precursor molecules appropriate for the practice of the present invention include monoacylglyerols (monoglycerides), diacylglycerols (diglycerides), and glycosylacylglycerols, each of which has one or more pendant —OH groups.

Each of the above precursor molecules has one or more groups, typically amine, hydroxyl and/or thiol groups, which allow them to be converted, using the procedures discussed above, into the S-nitroso- N-nitroso- and/or O-nitroso-compounds of the present invention.

As a specific example, an S-nitroso-N,N,N-trimethylsphingosine molecule is formed by first forming a thiol group at one or more of the hydroxyl groups of N,N,N-trimethylsphingosine, for example, using techniques such as those discussed above. The thiolated compound is subsequently nitrosylated using nitrosylating agents such as those described above. Upon delivery to the body (e.g., to the vasculature) the S-nitroso-N,N,N-trimethylsphingosine of the present invention releases nitric oxide, which has numerous beneficial therapeutic effects as noted above. Since it contains N,N,N-trimethylsphingosine, this compound also inhibits platelet formation and prevents leukocyte-endothelial interactions, even after the release of NO from the compound.

One advantage that the S-nitrosylated, N-nitrosylated and O-nitrosylated lipids of the present invention have over other organic NO donors and inorganic NO donors is that they can be readily incorporated into cell membranes, promoting tissue uptake and enhancing tissue retention time.

Similarly, the S-nitrosylated, N-nitrosylated and O-nitrosylated lipids of the present invention have an affinity for lipid deposits in the body, for example, those lipid depositions within atherosclerotic plaques. This affinity allows for targeted NO release within such regions.

As another example, and as discussed further below, they can also be provided within liposomes, which are also effectively incorporated into cell membranes and lipid deposits. As a specific example, where genetic material such as DNA or RNA is incorporated into liposomes comprising the S-nitrosylated, N-nitrosylated and/or O-nitrosylated lipid of the present invention, the NO released from the S-nitrosylated, N-nitrosylated and/or O-nitrosylated lipid would act to dilate capillaries, enhancing tissue uptake of the liposomes and increasing the amount of liposome (and hence genetic material) that is delivered across the cell membrane and into the cytoplasm.

Moreover, specific cell types can be targeted, for example, by forming liposomes from lipids that further contain cell-binding domains directed to, for example, protein receptors on the cell surface.

The S-nitrosylated, N-nitrosylated and O-nitrosylated lipids of the present invention can be delivered to the body by essentially any vehicle appropriate for delivery of therapeutic agents.

For instance, in some embodiments of the present invention, the S-nitrosylated, N-nitrosylated and/or O-nitrosylated lipids of the present invention are simply adsorbed as a monolayer on the surface of polymer, metal or silica-based materials, with polymer materials being more preferred. In general a very smooth surface is required for the lipid groups to orient in a head-to-tail orientation (or vice versa) on a material surface. Such a surface can be achieved, for example, by machining the material of interest with a polisher or grinder.

In other embodiments, the S-nitrosylated, N-nitrosylated and/or O-nitrosylated lipids of the present invention are added to a liquid delivery vehicle that is based on one or more lipophilic and/or hydrophilic solvents. In general, a solvent system is selected to disperse or dissolve the lipid of the present invention.

The S-nitrosylated, N-nitrosylated and/or O-nitrosylated lipids of the present invention are typically soluble in lipophilic solvents. Lipophilic solvents appropriate for the practice of the present invention include ethanol as well as other biocompatible lipophilic solvents such as dimethylsulfoxide (DMSO), methylpyrrolidone, methanol, isopropyl alcohol and so forth. One drawback associated with lipophilic solvents, however, is that they commonly have some degree of cytotoxicity.

Hydrophilic solvents, particularly water, can also be used in connection with the present invention. In some instances, the S-nitrosylated, N-nitrosylated and/or O-nitrosylated lipids are also sufficiently amphiphilic such that they are dissolved or dispersed in the hydrophobic solvent at the desired concentration.

Alternatively, to assist with the dissolution/dispersion of the lipids of the present invention, emulsifying agents or other surfactants may be added, allowing lipid to be dispersed in the solvent system.

In other instances, liposomes or micelles are formed which contain the S-nitrosylated, N-nitrosylated and/or O-nitrosylated lipids of the present invention.

Micelles are formed in the appropriate solvent at a high, critical concentration of lipid in solution as is known in the art.

For example, liposomes (lipid vesicles) are formed when thin lipid films or lipid cakes are hydrated and stacks of liquid crystalline bilayers become fluid and swell. The hydrated lipid sheets detach during agitation and self-close to form large, multilamellar vesicles (LMV) which prevents interaction of water with the hydrocarbon core of the bilayer at the edges. Once these particles have formed, reducing the size of the particle requires energy input in the form of sonic energy (sonication) or mechanical energy (extrusion). Disruption of an LMV suspensions using sonic energy (sonication) typically produces small, unilamellar vesicles (SUV) with diameters in the range of 15-50 nm. Lipid extrusion is a technique in which the lipid suspension is forced through a filter with a defined pore size to yield particles having a diameter near the pore size of the filter used. Such methods for preparing and handling liposomes are well known and are found, for example, in the Avanti Polar Lipids, Inc. Catalog, Edition IV, the disclosure of which is hereby incorporated by reference (see also http://avantilipids.com).

In other embodiments of the present invention, a polymer matrix is provided as a delivery vehicle and the S-nitrosylated, N-nitrosylated and/or O-nitrosylated lipid of the present invention is provided within the polymer matrix. The polymer matrix may be either biodegradable or non-biodegradable.

Numerous matrix materials exist in the art and a list of preferred polymers follows: polycarboxylic acids, including polyacrylic acid, available as HYDROPLUS® (Boston Scientific Corporation, Natick, Mass.) and described in U.S. Pat. No. 5,091,205, the disclosure of which is hereby incorporated herein by reference, gelatin, polyvinylpyrrolidone, cross-linked polyvinylpyrrolidone, polyanhydrides including maleic anhydride polymers, polyamides, polyvinyl alcohols, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, polyvinyl acetates, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate, coatings from polymer dispersions such as polyurethane dispersions (BAYHDROL®, etc.), fibrin, collagen and derivatives thereof, polysaccharides such as celluloses, starches, dextrans, alginates and derivatives such as cellulose acetate and cellulose nitrate, and hyaluronic acid.

Blends and copolymers containing the above-listed polymers are also appropriate for the practice of the invention. Some exemplary copolymers include copolymers of vinyl monomers such as EVA (ethylene-vinyl acetate copolymer) and poloxamers, which are also known as polyethylenepolypropylene glycols.

A diversity of administrative routes can be used for the delivery of the S-nitrosylated, N-nitrosylated and/or O-nitrosylated lipids to the patient's body. Patients include animal patients, preferably mammals, and more preferably humans.

Preferred administrative routes are topical routes, direct injection routes, intravascular routes and implantation routes.

Topically, the S-nitrosylated, N-nitrosylated and/or O-nitrosylated lipids can be administered in the form of a spray, solution, lotion, gel, cream, ointment or other topical delivery vehicle known in the art.

Patches or bandages are also contemplated. For example, the S-nitrosylated, N-nitrosylated and/or O-nitrosylated lipid can be dissolved or suspended in a liquid delivery vehicle (including solutions, dispersions, lotions, gels, creams, ointments, etc.) and applied to a patch or bandage. Alternatively, the S-nitrosylated, N-nitrosylated and/or O-nitrosylated lipid can be directly adsorbed to the patch or bandage surface, or the lipid can be disposed within a polymer matrix (such as those set forth above) disposed on the patch or bandage.

The above sprays, lotions, gels, creams, ointments, patches or bandages can be applied to intact skin (for example, to effect transdermal delivery of the lipids, which can result in, for instance, skin warming due to the resultant vasodilatation). They can also be applied to broken skin (for example, to enhance wound healing).

The S-nitrosylated, N-nitrosylated and/or O-nitrosylated lipids can also be provided within the body using a number of additional administrative routes, including implantation, intravascular delivery and direct injection.

For instance, the S-nitrosylated, N-nitrosylated and/or O-nitrosylated lipids can be provided in the form of an implant, which can serve to locally or systemically deliver the lipid. Implants appropriate for use in connection with the present invention include soft tissue implants, bone implants and so forth. For example, the implant can consist entirely of a matrix material, such as those set forth above, or it can consist of a substrate coated with such a matrix material, or it can consist of a base material upon which the S-nitrosylated, N-nitrosylated and/or O-nitrosylated lipid is adsorbed. The implant is preferably bioresorbable following NO release.

For direct injection, the S-nitrosylated, N-nitrosylated and/or O-nitrosylated lipid can be provided in the form of a solution or dispersion. Suitable liquid media for this purpose include both lipophilic- and hydrophilic-solvent-based systems with hydrophilic-solvent-based systems being preferred.

For intravascular delivery, the S-nitrosylated, N-nitrosylated and/or O-nitrosylated lipid can be provided in connection with a variety of intravascular delivery devices, including vascular catheters (for example, balloon catheters, injection catheters or infusion catheters), guide wires, balloons, filters (for example, vena cava filters), stents, stent grafts, vascular grafts, aneurysm fillers (including GDC (Guglielmi detachable coils)) and intraluminal paving systems.

In some embodiments, the S-nitrosylated, N-nitrosylated and/or O-nitrosylated lipid is directly adsorbed to the surface of the intravascular device (e.g., a stent, catheter, etc.). Surfaces appropriate for adsorption of the S-nitrosylated, N-nitrosylated and/or O-nitrosylated lipid include those listed above.

In other embodiments, the intravascular device includes a matrix that is loaded with the S-nitrosylated, N-nitrosylated and/or O-nitrosylated lipid. The matrix can be, for example, one of the matrices listed above, with biocompatibility being an important consideration. If of sufficient structural integrity, the matrix can constitute the entire device. Alternatively, the matrix can constitute a portion of the device (such as a device component, a portion thereof, or a coating on the device).

In other embodiments, the S-nitrosylated, N-nitrosylated and/or O-nitrosylated lipid is provided in a liquid medium that is injected from the intravascular device into the vascular wall. Suitable injection media are discussed above. Devices suitable for intravascular injections include needle injection catheters.

In still other embodiments, the S-nitrosylated, N-nitrosylated and/or O-nitrosylated lipid is expressed in liquid form from an intravascular device such that it comes into contact with the vascular wall or blood. Suitable liquid media for this purpose include both lipophilic- and hydrophilic-solvent-based systems with hydrophilic-solvent-based systems being preferred. Suitable devices include infusion catheters.

One beneficial effect associated with providing the S-nitrosylated, N-nitrosylated and/or O-nitrosylated lipid of the present invention on the surface of an implant or intravascular medical device, it that the surface of the device is rendered less thrombogenic (and preferably non-thrombogenic), due to the release of nitric oxide. Moreover, using these devices, the S-nitrosylated, N-nitrosylated and/or O-nitrosylated lipids can be administered locally to the blood and/or tissue surrounding the device or implant, leading to one or more of the beneficial tissue effects noted herein.

In other embodiments of the present invention, an auxiliary therapeutic agent in addition to the S-nitrosylated, N-nitrosylated and/or O-nitrosylated lipid is provided. This provides, for example, a "double-edged" therapy in which one therapeutic effect is provided by the S-nitrosylated, N-nitrosylated and/or O-nitrosylated lipid, and another effect is provided by the auxiliary therapeutic agent.

A wide variety of auxiliary therapeutic agents, including genetic therapeutic agents, non-genetic therapeutic agents, and cells, can be used in conjunction with the S-nitrosylated, N-nitrosylated and/or O-nitrosylated lipids of the present invention:

Exemplary non-genetic therapeutic agents include:
  anti-thrombotic agents such as heparin, heparin derivatives, urokinase, and PPack (dextrophenylalanine proline arginine chloromethylketone);
  anti-inflammatory agents such as dexamethasone, prednisolone, corticosterone, budesonide, estrogen, sulfasalazine and mesalamine;
  antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;
  anesthetic agents such as lidocaine, bupivacaine and ropivacaine;
  anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;
  vascular cell growth promoters such as growth factors, including platelet-derived growth factor, transcriptional activators, and translational promoters;
  vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
  protein kinase and tyrosine kinase inhibitors (e.g., tyrphostins, genistein, quinoxalines);
  prostacyclin analogs;
  cholesterol-lowering agents;
  angiopoietins;
  antimicrobial agents such as triclosan, cephalosporins, aminoglycosides and nitrofurantoin;
  cytotoxic agents, cytostatic agents and cell proliferation affectors;
  vasodilating agents; and
  agents that interfere with endogenous vascoactive mechanisms.

Exemplary genetic therapeutic agents include:
  anti-sense DNA and RNA;
  DNA coding for:
    anti-sense RNA,
    tRNA or rRNA to replace defective or deficient endogenous molecules,
    angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor a, hepatocyte growth factor and insulin like growth factor,
    cell cycle inhibitors including CD inhibitors,
    thymidine kinase ("TK") and other agents useful for interfering with cell proliferation, and
    the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.
  Vectors of interest for delivery of genetic therapeutic agents include
    Plasmids
    Viral vectors such as adenovirus (AV), adenoassociated virus (AAV) and lentivirus
    Non-viral vectors such as lipids, liposomes and cationic lipids.
  Cells include cells of human origin (autologous or allogeneic), including stem cells, or from an animal source (xenogeneic), which can be genetically engineered if desired to deliver proteins of interest.

The lipid compounds of the present invention are useful in providing the following effects, based on the following known actions of nitric oxide:
  Anti-thrombotic effects. Nitric oxide is known to inhibit platelet activation, preventing thrombus formation. As a result, the S-nitrosylated, N-nitrosylated and/or O-nitrosylated lipids of the present invention are useful in the treatment of peripheral vascular disease and coronary disease (atherosclerosis) where clot formation is a problem.

Vasodilation effects. Nitric oxide causes smooth muscle cells to relax, dilating arteries and other blood vessels. This is important in maintaining proper blood flow during myocardial infarction, stroke, impotence, and peripheral circulation diseases (e.g., arising as complications of diabetes).

Anti-inflammatory effects. Nitric oxide prevents white blood cell adhesion (anti-platelet activity also contributes to this effect), rendering the S-nitrosylated, N-nitrosylated and/or O-nitrosylated lipids of the present invention good candidates in the treatment of inflammatory disease, including psoriasis (and other skin disorders), septic shock, arthritis, atherosclerosis, stroke, and so forth.

Cytotoxic effects. At high dosages, nitric oxide is cytotoxic and can be used to reduce populations of undesirable cells, such as cancer cells, bacterial cells (see, e.g., U.S. Pat. No.5,814,666) and cells present in atherosclerotic lesions.

Nitric Oxide prevents inflammation and promotes good blood circulation. Nitric oxide is also important in the formation of collagen in wound healing (see, e.g., M R Schaffer et al., "Nitric oxide regulates wound healing", *J Surg Res* 1996 Jun; 63(1):237-40, the disclosure of which is hereby incorporated by reference). If nitric oxide synthesis is prevented, wounds have few proliferating cells, and little collagen formation and capillary formation, thereby delaying the healing response (see, e.g., M N Ackay et al, "Effect of nitric oxide synthase inhibitor on experimentally induced burn wounds", *J Trauma* 2000 August;49(2):327-30, the disclosure of which is hereby incorporated by reference).

As a result, the S-nitrosylated, N-nitrosylated and/or O-nitrosylated lipids of the present invention provide a good means of delivering nitric oxide to a wound or to a diseased site associated with a dermatological condition. Dermatological conditions of interest include impetigo, epidermolysis bullosa, eczema, neurodermatitis, psoriasis, pruritis, erythema, hidradenitis suppurativa, warts, diaper rash, jock itch, and combinations thereof. See, e.g., U.S. Pat. No. 5,869,104, "Method for treating dermatological conditions including impetigo" and WO 00/53193A1 entitled "Pharmaceutical composition containing nitrate source and an acidifying agent for treating skin ischaemia", the disclosures of which are hereby incorporated by reference.

Nitric oxide is also useful in promoting proper healing after angioplasty procedures. For example, lower dosages of nitric oxide are known to promote smooth muscle cell relaxation, reduce smooth muscle cell proliferation, promote endothelial cell health, prevent platelet activation, and reduce inflammation, all of which effects tend to promote vascular health and proper healing (e.g., healing without the advent of restenosis), for example, in the wake of angioplasty procedures.

As noted above, the S-nitrosylated, N-nitrosylated and/or O-nitrosylated lipids of the present invention have an affinity for lipid deposits in the body, such as those within atherosclerotic plaques, allowing for targeted NO release within such regions. The lipids of the present invention can be supplemented by lipases, which are delivered to affect the lipid metabolism of the artery wall (see, e.g., K Hirata et al., "Regulated expression of endothelial cell-derived lipase", *Biochem Biophys Res Commun* 2000 May 27; 272(1):90-3, the disclosure of which is hereby incorporated by reference). The lipids of the present invention can also be supplemented by plaque degrading enzymes agents such as metalloproteinases, including collagenases, elastases and other enzymes that degrade the extracellular matrix.

Conversely, since the action of matrix degradation is important in the migration of smooth muscle cells, the S-nitrosylated, N-nitrosylated and/or O-nitrosylated lipids of the present invention can also be combined with inhibitors of the metalloproteinases (for example, halofuginone which inhibits matrix metalloproteinase-2 expression and collagen expression). In this way, restenosis following angioplasty can be hindered by inhibiting the migration of smooth muscle cells.

As a treatment for restenosis following stent implantation or angioplasty (as well as other purposes), numerous auxiliary therapeutic agents can be supplied along with the S-nitrosylated, N-nitrosylated and/or O-nitrosylated lipids of the present invention. These include the following (several of which are also found in the above list of auxiliary therapeutic agents):

Other non-lipid nitric oxide donors
Platelet derived growth factor receptor antagonists
Tumor necrosis factor-alpha inhibitors
Ca-channel blockers including:
  Benzothiazapines such as diltiazem and clentiazem
  Dihydropyridines such as nifedipine, amlodipine and nicardapine
  Phenylalkylamines such as verapamil
Serotonin pathway modulators including:
  5-HT antagonists such as ketanserin and naftidrofuryl
  5-HT uptake inhibitors such as fluoxetine
Cyclic nucleotide pathway agents including:
  Phosphodiesterase inhibitors such as cilostazole and dipyridamole
  Adenylate/Guanylate cyclase stimulants such as forskolin
  Adenosine analogs
Catecholamine modulators including:
  α-antagonists such as prazosin and bunazosine
  β-antagonists such as propranolol
  α/β-antagonists such as labetalol and carvedilol
Endothelin receptor antagonists
Nitric oxide donors/releasing molecules including:
  Organic nitrates/nitrites such as nitroglycerin, isosorbide dinitrate and amyl nitrite
  Inorganic nitroso compounds such as sodium nitroprusside
  Sydnonimines such as molsidomine and linsidomine
  Nonoates such as diazenium diolates and NO adducts of alkanediamines
  S-nitroso compounds including low molecular weight compounds (e.g., S-nitroso derivatives of captopril, glutathione and N-acetyl penicillamine), high molecular weight compounds (e.g., S-nitroso derivatives of proteins, peptides, oligosaccharides, polysaccharides, synthetic polymers/oligomers and natural polymers/oligomers)
  C-nitrosothiols and N-nitrosothiols
  L-arginine
ACE inhibitors such as cilazapril, fosinopril and enalapril
ATII-receptor antagonists such as saralasin and losartin
Platelet adhesion inhibitors such as albumin and polyethylene oxide
Platelet aggregation inhibitors including:
  Aspirin and thienopyridine (ticlopidine, clopidogrel)
  GPIIb/IIIa inhibitors such as abciximab, epitifibatide and tirofiban Coagulation pathway modulators including:
  Heparinoids such as heparin, low molecular weight heparin, dextran sulfate and β-cyclodextrin tetradecasulfate
  Thrombin inhibitors such as hirudin, hirulog, PPACK (D-phe-L-propyl-L-arg-chloromethylketone) and argatroban
  FXa inhibitors such as antistatin and TAP (tick anticoagulant peptide)
  Vitamin K inhibitors such as warfarin
  Activated protein C
Cyclooxygenase pathway inhibitors such as aspirin, ibuprofen, flurbiprofen, indomethacin and sulfinpyrazone
Natural and synthetic corticosteroids such as dexamethasone, prednisolone, methprednisolone and hydrocortisone
Lipoxygenase pathway inhibitors such as nordihydroguairetic acid and caffeic acid
Leukotriene receptor antagonists
Anatgonists of E- and P-selectins
Inhibitors of VCAM-1 and ICAM-1 interactions
Prostaglandins and analogs thereof including:
  Prostaglandins such as PGE1 and PG12
  Prostacylcin analogs such as ciprostene, epoprostenol, carbacyclin, iloprost and beraprost
Macrophage activation preventers including bisphosphonates
HMG-CoA reductase inhibitors such as lovastatin, pravastatin, fluvastatin, simvastatin and cerivastatin
Fish oils and omega-3-fatty acids
Free-radical scavengers/antioxidants such as probucol, vitamins C and E, ebselen, trans-retinoic acid and SOD mimics
Agents affecting various growth factors including:
  FGF pathway agents such as bFGF antibodies and chimeric fusion proteins
  PDGF receptor antagonists such as trapidil
  IGF pathway agents including somatostatin analogs such as angiopeptin and ocreotide
  TGF-β pathway agents such as polyanionic agents (heparin, fucoidin), decorin, and TGF-β antibodies
  EGF pathway agents such as EGF antibodies, receptor antagonists and chimeric fusion proteins
  TNF-α pathway agents such as thalidomide and analogs thereof
  Thromboxane A2 (TXA2) pathway modulators such as sulotroban, vapiprost, dazoxiben and ridogrel
  Protein tyrosine kinase inhibitors such as tyrphostin, genistein and quinoxaline derivatives
MMP pathway inhibitors such as marimastat, ilomastat and metastat
Cell motility inhibitors such as cytochalasin B
Antiproliferative/antineoplastic agents including:
  Antimetabolites such as purine analogs (e.g., 6-mercaptopurine, thioguanine), pyrimidine analogs (e.g., cytarabine and 5-fluorouracil) and methotrexate
  Nitrogen mustards, alkyl sulfonates, ethylenimines, antibiotics (e.g., daunorubicin, doxorubicin), nitrosoureas and cisplatin
  Agents affecting microtubule dynamics (e.g., vinblastine, vincristine, coichicine, paclitaxel and epothilone)
  Caspase activators
  Proteasome inhibitors
  Angiogenesis inhibitors (e.g., endostatin, angiostatin and squalamine)
  Rapamycin, cerivastatin, flavopiridol and suramin Matrix deposition/organization pathway inhibitors such as halofuginone or other quinazolinone derivatives and tranilast
Endothelialization facilitators such as VEGF and RGD peptide
Blood rheology modulators such as pentoxifylline.

Dosages of the S-nitrosylated, N-nitrosylated and/or O-nitrosylated lipids of the present invention, as well as any ancillary therapeutic agents, will depend, for example, upon the lipids/therapeutic agents selected, upon the route of delivery, upon the condition being treated/prevented, upon the age of the patent, and so forth. It is well within the skill of those of ordinary skill in the art to make such determinations.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A nitric oxide releasing compound which is a lipid molecule comprising a phosphoglyceride and a nitric-oxide containing group selected from:
(a) a —S—N=O moiety, (b) a —O—N=O moiety, or (c) a

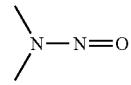

moiety.

2. The molecule of claim 1, wherein the phosphoglyceride is phosphatidylinositol or phosphatidylcholine.

3. The compound of claim 1, wherein said nitric-oxide containing group comprises a —S—N=O moiety.

4. The compound of claim 1, wherein said nitric-oxide containing group comprises a —O—N=O moiety.

5. The compound of claim 1, wherein said nitric-oxide containing group comprises a

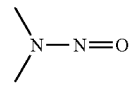

moiety.

6. The compound of claim 5, wherein said nitric-oxide containing group comprises a

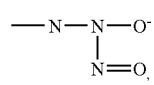

moiety.

7. The compound of claim 6, wherein said nitric-oxide containing group comprises a

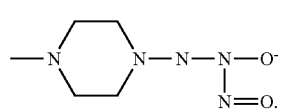

moiety.

8. A pharmaceutical composition comprising at least 0.001 wt % of the compound of claim 1.

9. A pharmaceutical composition comprising at least 0.01 wt % of the compound of claim 1.

10. A pharmaceutical composition comprising at least 0.1 wt % of the compound of claim 1.

11. A pharmaceutical composition comprising at least 1 wt % of the compound of claim 1.

12. A pharmaceutical composition comprising at least 10 wt % of the compound of claim 1.

13. A pharmaceutical composition comprising at least 90 wt % of the compound of claim 1.

14. A method of forming a nitric oxide releasing lipid molecule comprising: providing a lipid molecule having a nucleophilic moiety selected from a thiol moiety, an amine moiety, and an alcohol moiety, said lipid molecule being a phosphoglyceride, and supplying said lipid molecule with a nitric-oxide containing group at a position corresponding to said nucleophilic moiety, said nitric oxide containing group comprising a (a) a —S—N=O moiety, (b) a —O—N=O moiety, or

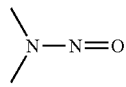

moiety.

15. The method of claim 14, wherein said nitric-oxide containing group comprises a —S—N=O moiety.

16. The method of claim 14, wherein said nitric-oxide containing group comprises a —O—N=O moiety.

17. The method of claim 14, wherein said nitric-oxide containing group comprises

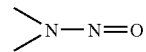

a moiety.

18. The method of claim 17, wherein said nitric-oxide containing group comprises

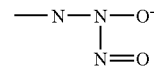

a moiety.

19. The method of claim 14, wherein an alcohol moiety on said lipid molecule is converted to a group comprising a thiol moiety prior to supplying said lipid molecule with said nitric-oxide containing group.

20. The method of claim 19, wherein an —S—N=O moiety is formed on said lipid molecule at a position corresponding to said thiol moiety.

21. A topical liquid comprising the compound of claim 1.

22. A topical liquid selected from the group consisting of a solution, a dispersion, a spray, a lotion, a gel, a cream and an ointment, said topical liquid comprising the compound of claim 1.

23. A liposome comprising the compound of claim 1.

* * * * *

UNITED STATES PATENT AND TRADEMARK OFFICE
CERTIFICATE OF CORRECTION

PATENT NO. : 7,696,247 B2 Page 1 of 1
APPLICATION NO. : 10/885055
DATED : April 13, 2010
INVENTOR(S) : Herrmann et al.

It is certified that error appears in the above-identified patent and that said Letters Patent is hereby corrected as shown below:

Col. 12, line 31, after "factor" change "a" to "α".

Signed and Sealed this

Thirteenth Day of July, 2010

David J. Kappos
*Director of the United States Patent and Trademark Office*